United States Patent [19]
Seshimoto et al.

[11] Patent Number: 4,789,435
[45] Date of Patent: * Dec. 6, 1988

[54] METHOD AND DEVICE OF MEASURING ION ACTIVITY

[75] Inventors: Osamu Seshimoto; Yoshio Saito, both of Asaka, Japan

[73] Assignee: Fuji Photo Film Co., Ltd., Kanagawa, Japan

[*] Notice: The portion of the term of this patent subsequent to Aug. 4, 2004 has been disclaimed.

[21] Appl. No.: 896,888

[22] Filed: Aug. 14, 1986

[30] Foreign Application Priority Data

Aug. 15, 1985 [JP] Japan .................................. 60-180358
Aug. 15, 1985 [JP] Japan .................................. 60-180359
Aug. 15, 1985 [JP] Japan .................................. 60-180360

[51] Int. Cl.$^4$ .............................................. G01N 27/30
[52] U.S. Cl. .................................. 204/1 T; 204/411; 204/412; 204/416
[58] Field of Search ............... 204/1 T, 416, 418, 412, 204/411; 422/68, 99

[56] References Cited

U.S. PATENT DOCUMENTS 3,770,608 11/1973 Kelch ..................... 204/416
4,273,639 6/1981 Gottermeier ............ 204/416
4,578,173 3/1986 Seshimoto ............... 204/416
4,684,445 8/1987 Seshimoto ............... 204/416

Primary Examiner—John F. Niebling
Assistant Examiner—Ben C. Hsing
Attorney, Agent, or Firm—Jules E. Goldberg

[57] ABSTRACT

In a method of measuring ion activity of a liquid sample comprising steps of spotting a reference liquid and the liquid sample on surfaces of ion-selective membranes, respectively, of at least a pair of ion-selective electrode sheets which is electrically insulated from each other, said ion-selective membranes being provided on the top of said ion-selective electrode sheets; and measuring a potential difference between the ion-selective electrodes under the conditions that both liquids are electrically connected to each other by a bridge, the improvement wherein:

said each ion-selective electrode sheet is arranged upside down in such a manner that the ion-selective membrane is positioned on the lowest side; and said each liquid spotted from the upper side is temporarily conveyed downwardly to the lower level than the surface of the ion-selective membrane or the spotting is done on the lower level than the surface of the ion-selective membrane, and then conveyed upwardly to the surface of the ion-selective membrane through an upward passage which has a side wall being clear of the surface of the ion-selective membrane under the condition that no capillary phenomenon occurs in the clearance between the top of said side wall and the surface of the ion-selective membrane, so as to reach the surface of the ion-selective membrane.

22 Claims, 10 Drawing Sheets

FIG. I
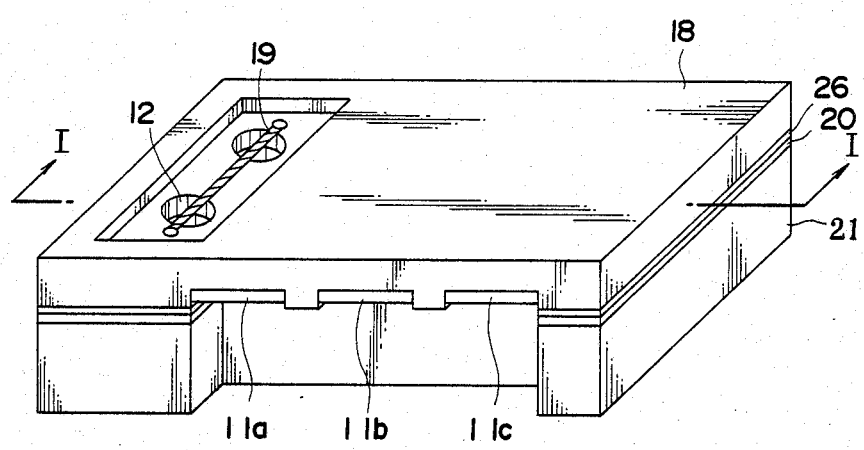
FIG. IA
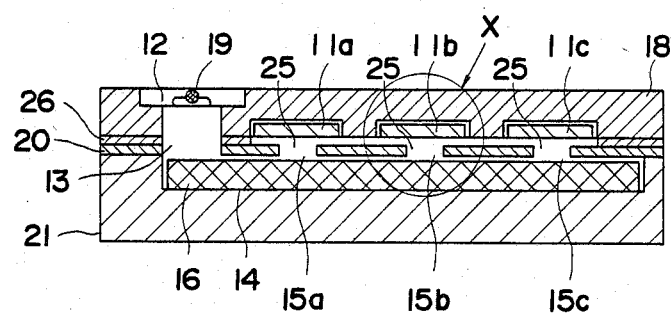

FIG.2
FIG.3
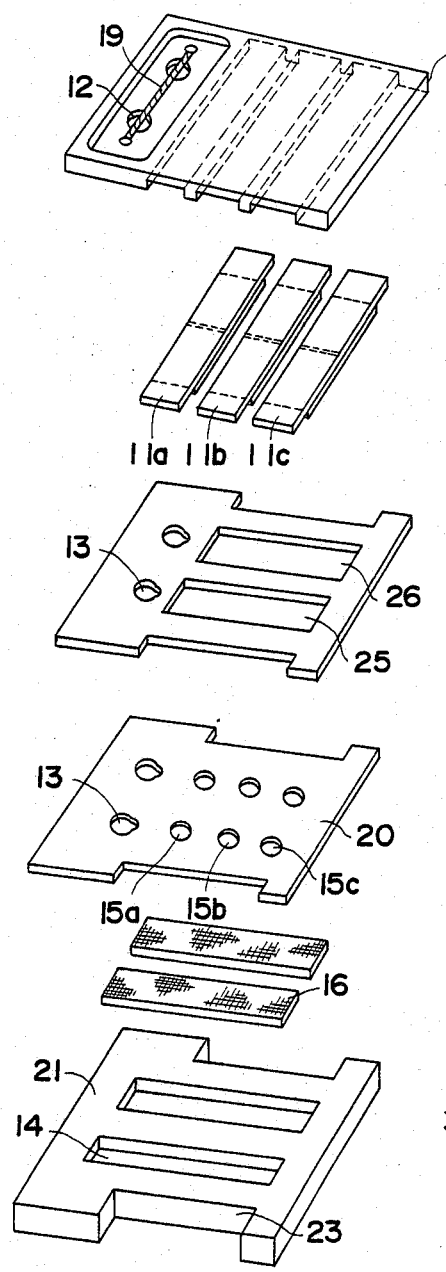
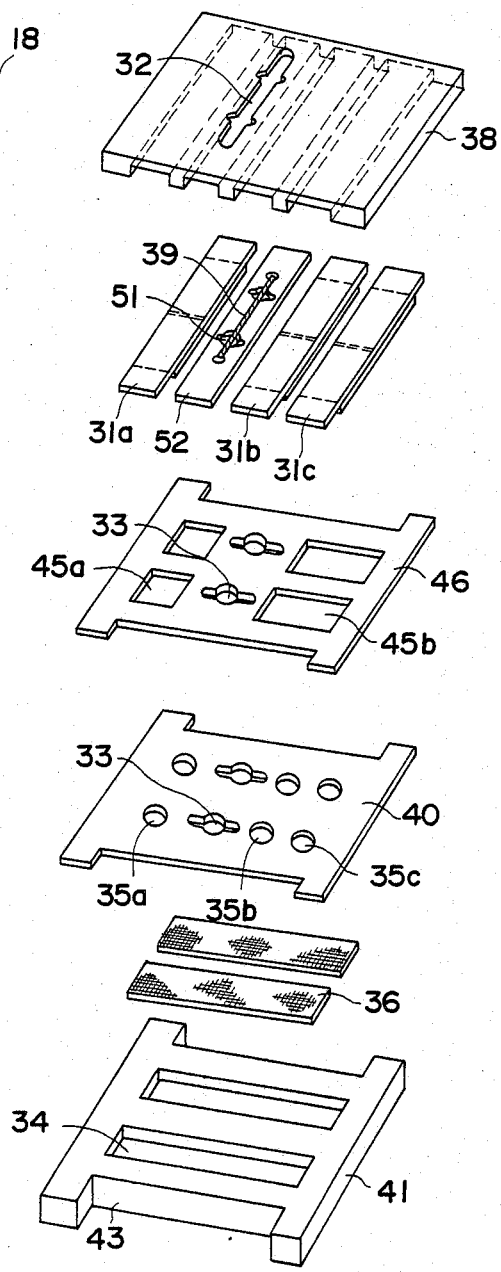

METHOD AND DEVICE OF MEASURING ION ACTIVITY

BACKGROUND OF THE INVENTION

1. Field of the Invention

The present invention relates to a method of measuring ion activity for the quantitative analysis of specific ion activity (or ion concentration) contained in an aqueous liquid, particularly a body fluid such as blood, urine or saliva, utilizing potentiometry, and a measuring device employable in said method

2. Description of Prior Arts

There has been known a method of measuring specific ion activity contained in a liquid sample of an aqueous liquid (e.g., tap water, river water, sewage or industrial drainage) and a body fluid (e.g., blood such as whole blood, plasma and serum; urine, or saliva) by using an ion activity measuring device in the form of sheet.

In the method, a reference liquid and a liquid sample are spotted onto surfaces of ion-selective membranes, respectively, which are arranged on the top of at least a pair of ion-selective electrode sheets, and then potential difference between the ion-selective electrodes is measured under the condition that both liquids are electrically connected to each other by means of a bridge, so as to determine the ion activity of the liquid sample.

Examples of the ion activity measuring device employable in the method are described, for instance, in Japanese Patent Provisional Publications No. 52 (1977)-142586 (corresponding to U.S. Pat. No. 4,053,381), No. 56(1981)-6148 (corresponding to U.S. Pat. No. 4,273,639) and No. 58(1983)-211648 (corresponding to U.S. Pat. No. 4,437,970). In these devices, a pair of ion-selective electrode sheets are arranged in such a manner that ion-selective membranes are positioned on the upper side, and on the ion-selective membranes are provided liquid receiving openings (openings for allowing introduction of a reference liquid and a liquid sample). In practically determining the ion activity by the use of those devices, the reference liquid and liquid sample are spotted onto the ion-selective membranes through the liquid receiving openings using a pipet, etc., and a potential difference between both ion-selective electrodes is measured. As an improved device, there is known a device comprising a plurality of pairs of ion-selective electrodes, which can determine ion activity of plural kinds of ions by only once spotting of a reference liquid and a liquid sample thereonto.

The above-described method using at least one pair of ion-selective electrode sheets is an easy and advantageous method for determining ion activity, but the present inventors have found that there are various problems not only in the preparation of the measuring device but also in the measuring operation.

For instance, as the first problem, an ion-selective membrane of the ion-selective electrode is easily damaged by a tip of a pipet which is generally employed for spotting a reference liquid or a liquid sample. Since the ion-selective membrane is not solid but like a jelly, the membrane is easily damaged or distorted when the tip of pipet comes into contact with the surface of the membrane. Such deterioration of the shape of the ion-selective membrane brings about an error in the determination of ion activity, and in an extreme case, the determination thereof becomes impossible.

As the second problem, a silver chloride layer of the ion-selective electrode is easily deteriorated. Most of the ion-selective electrodes utilize a silver/silver chloride electrode (i.e., half cell) as an inner reference electrode. In this case, if the ion activity measuring device is allowed to stand in a light room, the silver chloride layer is denatured by a light entering from the liquid receiving opening, whereby the electrode is deteriorated.

As the third problem, a probe which serves to measure the potential difference occurring between the ion-selective electrodes is apt to be stained. An ion-selective electrode sheet is generally employed in a form comprising a plastic sheet support and an electrode placed on the surface thereof. In determining the ion activity by the use of the ion-selective electrode sheet, it is necessary to measure the potential difference between a pair of ion-selective electrodes as described hereinbefore. Accordingly, at the ends of the electroconductive portion of the ion-selective electrode (e.g., a silver layer of a silver/silver chloride electrode) are provided electricity-connecting regions (e.g., elongations of the silver layer). The electricity-connecting regions are brought into contact with the aforementioned probes of the potential difference measuring device which is prepared separately so as to determine the potential difference. When the ion-selective membrane is placed on the upper side as in the conventional device, the surface of the electricity-connecting region naturally faces to the upper side, and the probe of the potential difference measuring device is brought from the upper side into contact with the surface of the electrically connecting region. Accordingly, the probe tends to be stained with the reference liquid or liquid sample which is introduced from the same upper side.

As the fourth problem, the measuring system of the potential difference measuring device used in combination with the ion activity measuring device becomes complicated. In more detail, if the ion-selective membrane is placed on the top, the surface of the electrically-connecting region faces to the upper side, and accordingly the probe of the potential difference measuring device is necessarily arranged to contact on the upper side with the surface of the electrically connecting region, as described above. In such arrangement, in order to obtain smooth electric wiring between the probe of the potential difference measuring device and an amplifier such as a head amplifier settled in the vicinity of the prove, the electric wiring is required to be made on the upper side of the device or in the side direction of the device. However, it is generally advantageous to arrange the probe of the potential difference measuring device below the ion activity measuring device, from the viewpoint of preventing the probe from the contact with the reference liquid or liquid sample or saving the space required for settling the devices. In utilizing the conventional ion activity measuring device which is formulated to be used in the system that an ion-selective membrane is placed on the upper side and a reference liquid or a liquid sample is spotted on the membrane, the measuring system of the potential difference measuring device used in combination with the ion activity measuring device becomes complicated, and a large space is required for the measuring system.

As the fifth problem, there is a difference between times required for a reference liquid or a liquid sample reaching the surface of each electrode in measuring plural kinds of ion activity using the conventional measuring system. Further, there is also a difference between spotting areas. Said differences are factors of errors in measurement.

SUMMARY OF THE INVENTION

It is an object of the present invention to provide a method of measuring ion activity of one or plural kinds of ions using one ion activity measuring device, and ion activity measuring devices which are advantageously employed in said method.

Specifically, the present invention has an object to provide a method of measuring ion activity which is almost free from the above-described various problems attached to the conventional method, and an ion activity measuring device advantageously employed in the method.

The present invention provides a method of measuring ion activity of a liquid sample which comprises steps of spotting a reference liquid and the liquid sample on surfaces of ion-selective membranes, respectively, of at least a pair of ion-selective electrode sheets which are electrically insulated from each other, said ion-selective membranes being arranged on the top of said ion-selective electrode sheets; and measuring a potential difference between the ion-selective electrodes under the condition that said both liquids are electrically connected to each other by a bridge, which is characterized in that:

said each ion-selective electrode sheet is arranged upside down in such a manner that the ion-selective membrane is positioned on the lowest side; and said each liquid spotted from the upper side is temporarily conveyed downwardly to the lower level than the surface of the ion-selective membrane or the spotting is done on the lower level than the surface of the ion-selective membrane, and then conveyed upwardly to the surface of the ion-selective membrane through an upward passage which has a side wall being clear of the surface of the surface of the ion-selective membrane under the condition that no capillary phenomenon occurs in the clearance between the top of said side wall and the surface of the ion-selective membrane, so as to reach the surface of the ion-selective membrane.

The above-mentioned method of the invention can be advantageously performed using an ion activity measuring device which comprises at least a pair of ion-selective electrode sheets having ion-selective membranes on the top, liquid-guiding portions for guiding a reference liquid and a liquid sample onto each surface of said ion-selective membranes, respectively, and a bridge for electrically connecting both liquids to each other, which is characterized in that:

said each ion-selective electrode sheet is arranged upside down in such a manner that the ion-selective membrane is positioned on the lowest side; and said each liquid-guiding portion comprises a liquid receiving opening for supplying the liquid to the lower place than the surface of the ion-selective membrane, a horizontal passage for conveying said liquid in the horizontal direction to a position just below the surface of the ion-selective membrane, and an upward passage for conveying the liquid upwardly to the surface of the ion-selective membrane, said upward passage having a side wall being clear of the surface of the ion-selective membrane under the condition that no capillary phenomenon occurs in the clearance between the top of said side wall and the surface of the ion-selective membrane.

In the above-mentioned device of the invention, a spotting guide passage may be provided on the upper side of the upward passage. The spotting guide passage has both functions of guiding the liquid to the surface of the ion-selective membrane and of preventing the liquid which has reached the surface of the ion-selective membrane from spreading to the side of the ion-selective membrane along said surface. The top of the side wall of the spotting guide passage may be in contact with the surface of the ion-selective membrane.

The ion activity measuring device which does not have said spotting guide passage is hereinafter named a first embodiment of the invention. The device which has said spotting guide passage, the top of the side wall of said spotting guide passage not being in contact with the surface of the ion-selective membrane, is hereinafter named a second embodiment of the invention. The device which has said spotting guide passage, the top of the side wall of said spotting guide passage being in contact with the surface of the ion-selective membrane, is hereinafter named a third embodiment of the invention.

The expression "clearance in which no capillary phenomenon occurs" means that the clearance is so large that the liquid can not enter the space between the top of said side wall and the surface of the ion-selective membrane. The size of the above-mentioned clearance is usually 50 $\mu$m or more, but the size is affected by the surface tension of the liquid, the quality or state of the surface material with which the liquid will contact.

By the use of the method and device of the present invention, the aforementioned various problems inherently attached to the conventional method and device can be obviated.

That is, for the first and second probrems, physical deterioration of the ion-selective membrane of the ion-selective electrode caused by the contact with a tip of a pipet and chemical deterioration of the electrode portion of the ion-selective electrode caused by exposure to light can be effectively prevented using the method and device of the invention.

For the third and forth problems, since the surface of the electrically connecting region is arranged to face to the lower side according to the invention, the electric wiring can be made smoothly between the the probe of the potential difference measuring device arranged on the lower side against the liquid-guiding system of the upper side and the head amplifier placed in its vicinity. Accordingly, the probe of the potential difference measuring device can be prevented from being stained with the liquid, and the measuring system of potential difference can be made simple.

For the fifth problem, since the side wall of the upward passage is provided clear of the surface of the ion-selective membrane under the condition that no capillary phenomenon occurs in the clearance between the top of said side wall and the surface of the ion-selective membrane according to the invention, the periods of time required for a reference liquid or a liquid sample reaching the surface of each electrode can be made uniform. Further, the spotting area can be also made uniform. Further more, even when an oily substance is used in the ion-selective membrane, the substance is not in contact with the top of said side wall and prevented from flowing out, so that the uniform distribution of the substance can be preserved.

When the spotting guide passage is provided on the upper side of the upward passage in the device of the invention, the spotting area can be made exactly uniform. Accordingly, errors in measurement caused by the difference between spotting areas can be prevented by the spotting guide passage.

In addition, the ion-selective electrode sheet and the frames therefor are hardly distorted in the preparation of the ion activity measuring device of the present invention. As a result, a device capable of measuring ion activity with high accuracy can be obtained.

BRIEF DESCRIPTION OF THE DRAWINGS

FIG. 1-A is an elevational section of the ion activity measuring device of FIG. 1 taken along line I-I; FIG. 1-B is a bottom view of the ion activity measuring device of FIG. 1; FIG. 1-C is an enlarged view of a portion X enclosed with a circle in the elevational section of FIG. 1-A; and FIG. 1-D is an enlarged view illustrating the liquid coming into contact with the ion-selective electrode.

FIG. 2 shows each member of the ion activity measuring device of FIG. 1, in order to illustrate each member constituting the ion activity measuring device in more detail.

FIG. 3 shows each member of another example of the ion activity measuring device according to the first embodiment of the invention likewise in FIG. 2.

FIG. 5-B is a perspective view illustrating a porous distributor used in FIG. 5-A.

FIG. 6-B is an enlarged view of a portion X enclosed with a circle in the elevational section of FIG. 6-A; FIG. 6-C is an enlarged view illustrating one state that the liquid is coming into contact with the ion-selective electrode; FIG. 6-D is an enlarged view illustrating another state that the liquid is coming into contact with the ion-selective electrode; and FIG. 6-E is a perspective view illustrating a spotting guide passage in the second embodiment of the invention.

FIG. 10-A is an elevational section of the ion activity measuring device of FIG. 10 taken along line I-I; FIG. 10-B is an enlarged view of a portion X enclosed with a circle in the elevational section of FIG. 10-A; and FIG. 10-C is an enlarged view illustrating the liquid coming into contact with the ion-selective electrode.

DETAILED DESCRIPTION OF THE INVENTION

The method and device of measuring ion activity of the present invention will be described more in detail hereinafter by referring to the ion activity measuring devices shown in the accompanying drawings.

Figure 1B:
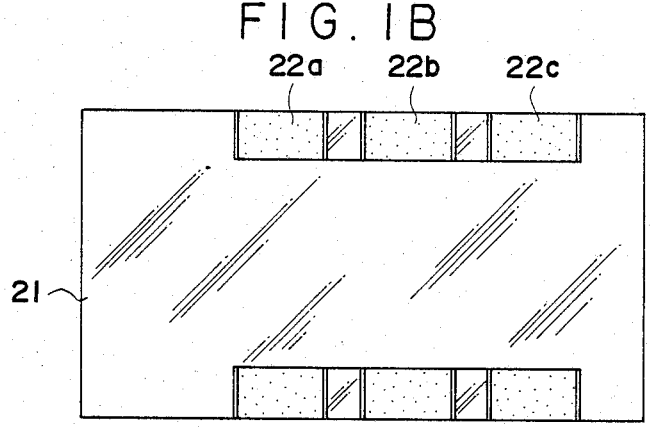
FIG. 1 is a perspective view illustrating an example of the ion activity measuring device according to the first embodiment of the invention.
Figure 1C:
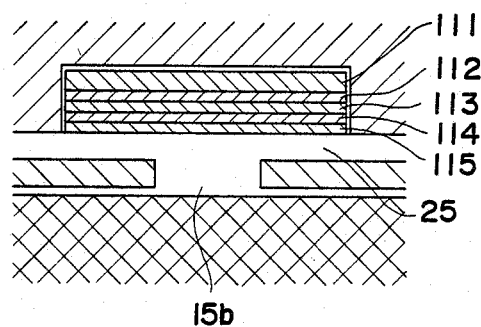
Figure 1D:
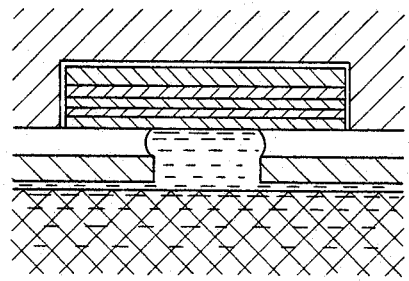

FIG. 1 is a perspective view illustrating an example of the ion activity measuring device according to the first embodiment of the invention. FIG. 1-A is an elevational section of the ion activity measuring device of FIG. 1 taken along line I—I; FIG. 1-B is a bottom view of the ion activity measuring device of FIG. 1; FIG. 1-C is an enlarged view of a portion X enclosed with a circle in the elevational section of FIG. 1-A; and FIG. 1-D is an enlarged view illustrating the liquid coming into contact with the ion-selective electrode.

FIG. 2 shows each member of the ion activity measuring device of FIG. 1, in order to illustrate each member constituting the ion activity measuring device in more detail.

In the ion activity measuring device shown in the above-described figures, three pairs of ion-selective electrode sheets $11a$, $11b$ and $11c$, each sheet comprising ion-selective membranes on the top portion, are arranged upside down in such a manner that the ion-selective membranes are arranged on the lowest side. Each pair of ion-selective electrodes is a combination of an ion-selective electrode for a reference liquid and an ion-selective electrode for a liquid sample which are electrically insulated from each other. The ion-selective electrode sheet comprises, for instance, a support of plastic sheet 111, a metallic silver-deposited layer 112, a silver chloride layer 113, an electrolyte layer 114 and an ion-selective membrane 115, superposed in this order, as shown in FIG. 1-C. The ion-selective electrode sheet having such structure is placed upside down in the ion activity measuring device.

As shown in FIG. 1-A, a liquid-guiding portion for guiding a reference liquid or a liquid sample to the surface of the ion-selective membrane comprises a liquid receiving opening 12 on the upper side, a downward passage 13 for conveying the liquid downwardly to the lower level under the surface of the ion-selective membrane, a horizontal passage 14 for conveying the liquid in the horizontal direction to the position just below the surface of the ion-selective membrane, and upward passages $15a$, $15b$ and $15c$ for conveying the liquid upwardly to the surface of the ion-selective membrane.

The upward passages $15a$, $15b$ and $15c$ have the side wall provided clear of the surface of the ion-selective membrane under the condition that no capillary phenomenon occurs in the clearance between the top of said side wall and the surface of the ion-selective membrane. As shown in FIG. 1-A and FIG. 1-C, space 25 which is larger than the upward passages 15a, 15b and 15c is provided on the upper side of the upward passage. As shown in FIG. 1-D, the liquid conveyed upwardly from the horizontal passage 14 then reaches the surface of the ion-selective membrane without capillary phenomenon. Accordingly, the liquid can be prevented from spreading on the surface of the ion-selective membrane caused by capillary phenomenon, so that the liquid can be also prevented from leaking out.

The space 25 is connected with all of the upward passages 15a, 15b and 15c. The space 25 may be made open to the outside of the device through a passage other than the upward passage in this invention.

For performing smooth conveyance of the liquid, the horizontal passage 14 is preferably equipped with a porous distributor 16 (namely, liquid-conveying member having continuous micropores capable of showing capillarity) such as cotton bandage fabric, cotton gauze or nonwoven fabric. The employment of the porous distributor is particularly advantageous especially when the amount of the reference liquid or liquid sample is small.

The three pairs of ion-selective electrodes 11a, 11b and 11c are contained in the top frame 18 of plastic material, and generally fixed to the top frame. The top frame 18 has openings 12 to receive spotting of liquid therethrough, and said two openings (opening for a reference liquid and an opening for a liquid sample) are traversed by a bridge 19 such as a combustible thread bridge of polyethylene terephthalate fiber (e.g., spun yarn) to electrically connect both liquids of the reference liquid and the liquid sample to each other.

Around each of the openings 12 is provided a protruded region (not shown in the figures) which serves to prevent the liquid from flowing over the opening and also serves to easily receive spotting the liquid without fail.

Under the top frame 18 is provided an upper middle frame (spacer) 26. In the upper middle frame 26, a part of the downward passage 13 for downwardly conveying the spotted liquid and the space 25 provided on the upper side against the upward passage are formed as opening portions.

Under the upper middle frame 26 is provided a lower middle frame 20 of water-impermeable sheet such as a mask of plastic material. In the lower middle frame 20, a part of the downward passage 13 for downwardly conveying the spotted liquid and the upward passages 15a, 15b and 15c are formed as opening portions. The upper middle frame 26 and the water-impermeable lower middle frame 20 are desired to be combined with the bottom surface of the top frame 18 by the use of an adhesive (e.g., pressure-sensitive adhesive or heat-sensitive adhesive) or through thermal bonding or physical engagement.

A bottom frame 21 of plastic material is arranged below the water-impermeable lower middle frame 20. The aforementioned horizontal passage 14 is formed in the bottom frame 21 as a groove. The horizontal passage 14 may be equipped with the aforementioned porous distributor 16, as desired. The porous distributor 16 may be fixed to the horizontal passage 14.

The bottom frame 21 has cutout portions 23 on the both sides to make each of the electricity-connecting regions 22a, 22b and 22c of the ion-selective electrodes 11a, 11b and 11c exposed in the downward direction (see FIG. 1-B). The cutout portions 23 may be formed in plural pairs to correspond to the plural pairs of ion-selective electrodes. Otherwise, one pair of cutout portions may be formed on the both sides of the device to expose the electrically connecting regions of all ion-selective electrodes. The latter embodiment is shown in FIG. 1-B.

The bottom frame 21 is preferably combined with the water-impermeable lower middle frame 20 by the use of an adhesive (e.g., pressure-sensitive adhesive or heat-sensitive adhesive) or by thermal bonding or physical engagement.

Whole of the top frame, upper middle frame, water-impermeable lower middle frame and bottom frame, or a part of those frames can be formed to give an integrated structure, as far as the ion-selective electrode and the porous distributor which is optionally employed can be contained therein. Each of the top frame, upper middle frame, lower middle frame and bottom frame is not always necessarily an integrated form, and can be composed of plural members.

Each of the top frame, upper middle frame, water-impermeable lower middle frame and bottom frame can be prepared using a desired self-supporting material. From the viewpoint of various properties such as moldability and shock impact resistance, those frames are preferably formed from plastic materials. For instance, those frames can be formed by a known method such as a molding method using a plastic material and a desired mold or a drawing method using a plastic sheet.

In the device for measuring ion activity shown in FIG. 1 and FIG. 2, the ion-selective electrode sheet is settled in a container comprising a top frame having opening portions which are located to correspond to each liquid receiving opening, an upper middle frame having opening portions which are located to correspond to each liquid receiving opening and to the upper opening of the upward passage, said opening portions corresponding to the upper opening of the upward passage being larger than said upper opening to avoid being in contact with the liquid, a water-impermeable lower middle frame having opening portions which are located to correspond to the downward and upward passages, and a bottom frame having a groove for forming the horizontal passage; and said bridge is fixed onto the top frame so as to traverse the opening portions of the top frame.

FIG. 3 shows each member of an ion activity measuring device which is another example of the devices according to the first embodiment of the invention, in order to illustrate each member constituting the ion activity measuring device in more detail, likewise in FIG. 2.

In the ion activity measuring device shown in FIG. 3, as well as in FIG. 2, three pairs of ion-selective electrode sheets 31a, 31b and 31c which are provided with ion-selective membranes on the top portion are arranged upside down to position the ion-selective membranes on the lowest side. The three pairs of ion-selective electrodes 31a, 31b and 31c are contained in a top frame 38 of plastic material, and generally fixed to the top frame. The top frame 38 has a liquid-receiving opening 32.

In the example of FIG. 3, the three pairs of ion-selective electrodes are divided into one pair and two pairs in the left side and the right side, respectively. The ion activity measuring device having such structure is very advantageous especially when a liquid having high viscosity such as whole blood is employed as a liquid sample, because the distance between the opening 32 and the farthest ion-selective electrode therefrom is shorter as compared with the device shown in FIGS. 1 and 2.

Under the top frame 38 is placed a bridge-supporting member 52 of plastic material having two opening portions 51 in such a manner that the two opening portions 52 are located to correspond to the liquid receiving opening 32. The two opening portions are traversed by a bridge 39 to electrically connect both liquids of reference liquid and liquid sample spotted to the opening portions to each other. The bridge-supporting member of plastic material shown in FIG. 3 has substantially the same size as that of the above-mentioned one pair of ion-selective electrode.

Under the bridge-supporting member 52 is provided an upper middle frame 46. In the upper middle frame sheet 46, a part of a downward passage 33 for conveying a liquid downwardly and the space 45a and 45b provided on the upper side against the upward passage are formed as opening portions.

Under the upper middle frame 46 is provided a lower middle frame 40 of water-impermeable sheet such as a mask of plastic material. In the water-impermeable middle frame sheet 40, a part of a downward passage 33 for conveying a liquid downwardly and upward passages 35a, 35b and 35c are formed to give opening portions. The details of the space 45a, 45b and the upward passages 35a, 35b and 35c are similar to that shown in FIG. 1 to FIG. 1-D. The upper middle frame 46 and the water-impermeable lower middle frame 40 are preferably combined with the lower surfaces of the bridge-supporting member 52 and the top frame 38 by the use of an adhesive (e.g., pressure-sensitive adhesive or heat-sensitive adhesive) or through thermal bonding or physical engagement.

A bottom frame 41 of plastic material is placed below the water-impermeable lower middle frame sheet 40. A horizontal passage 34 is formed in the bottom frame 41 as a groove. The horizontal passage 34 may be equipped with a porous distributor 36, as desired. The porous distributor 36 may be fixed to the horizontal passage 34.

The bottom frame 41 has cutout portions 43 on the both sides to make each of the electricity-connecting regions of the ion-selective electrodes 31a, 31b and 31c exposed in the downward direction (see FIG. 1-B).

The bottom frame 41 is desired to be combined with the water-impermeable middle frame 40 by the use of an adhesive (e.g., pressure-sensitive adhesive or heat-sensitive adhesive), or through thermal bonding or physical engagement.

Whole of the top frame, bridge-supporting member, upper middle frame and water-impermeable lower middle frame, or a part of those frames can be formed as an integrated structure, as far as the ion-selective electrode and the porous distributor which is optionally employed can be contained therein. Each of the top frame, upper middle frame, lower middle frame and bottom frame can be composed of plural members, and any material can be optionally employed for those frames, as well as in the aforementioned example.

In the device for measuring ion activity shown in FIG. 3, the ion-selective electrode sheet is settled in a container comprising a top frame having opening portions which are located to correspond to each liquid receiving opening, a bridge-supporting member having opening portions which are located to correspond to the opening portions of the top frame, an upper middle frame having opening portions which are located to correspond to each liquid receiving opening and to the upper opening of the upward passage, said opening portions corresponding to the upper opening of the upward passage being larger than said upper opening to avoid being in contact with the liquid, a water-impermeable lower middle frame having opening portions which are located to correspond to the downward and upward passages, and a bottom frame having a groove for forming the horizontal passage; and said bridge is fixed onto the bridge-supporting member so as to traverse the opening portions of the bridge-supporting member.

In the case of ion activity measuring device illustrated in FIG. 3, since the top frame and the bridge-supporting member are formed separately as stated above, each of those members has a simple structure, and hence it can be easily prepared.

Further, in the figure a thread bridge is fixed not to the top frame but to an independent bridge-supporting sheet (namely, bridge-supporting member) in the device shown in FIG. 3, and accordingly the top frame is not distorted in the procedure of thermal bonding with the thread bridge so as not to give the distortion to the ion-selective electrode. As a result, an ion activity measuring device can be prepared with high accuracy, whereby a device with high accuracy is obtained.

Figure 4:
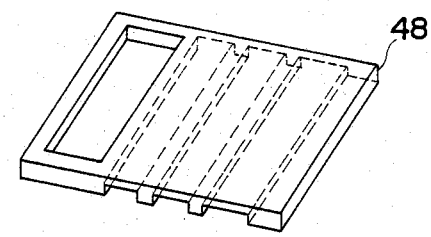
FIG. 4 shows each member of a further example of the ion activity measuring device according to the first embodiment of the invention likewise in FIG. 2 and 3.
Figure 4:
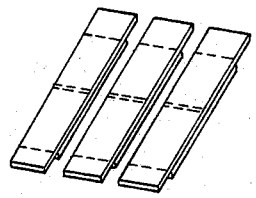
Figure 4:
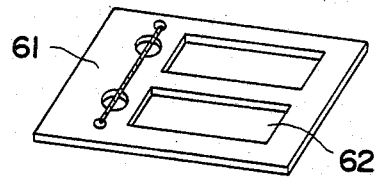
Figure 4:
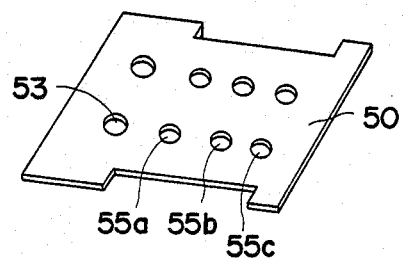
Figure 4:
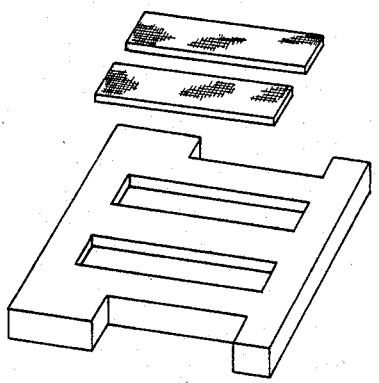

FIG. 4 shows each member of an ion activity measuring device which is a further example of the devices according to the first embodiment of the invention, in order to illustrate each member constituting the ion activity measuring device in more detail, likewise in FIG. 2 and FIG. 3.

In the case of ion activity measuring device illustrated in FIG. 4, the top frame 48 and the bridge-supporting member 61 are formed separately likewise in the example shown in FIG. 3.

The bridge-supporting member 61 provides large space 62 corresponding to the space 25 shown in FIG. 1 to FIG. 2. Accordingly, there is only one middle frame in example shown in FIG. 4, which is the water-impermeable middle frame 50 having opening portion 53 corresponding to the downward passage and other opening portions 55a, 55b and 55c corresponding to the upward passages.

In the device for measuring ion activity shown in FIG. 4, the ion-selective electrode sheet is settled in a container comprising a top frame having opening portions which are located to correspond to each liquid receiving opening, a bridge-supporting member having opening portions which are located to correspond to each liquid receiving opening and to the upper opening of the upward passage, said opening portions corresponding to the upper opening of the upward passage being larger than said upper opening to avoid being in contact with the liquid, a water-impermeable middle frame having opening portions which are located to correspond to the downward and upward passages, and a bottom frame having a groove for forming the horizontal passage; and said bridge is fixed onto the bridge-supporting member so as to traverse the opening portions of the bridge-supporting member.

Figure 5A:
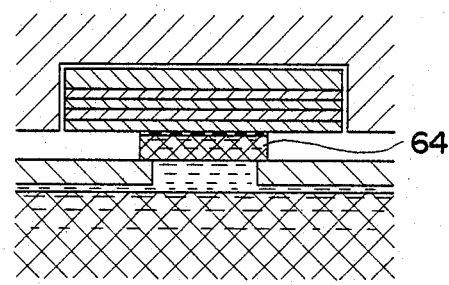
FIG. 5-A is an enlarged view illustrating the liquid coming into contact with the ion-selective electrode in a still further example of the ion activity measureing device according to the first embodiment of the invention.
Figure 5B:
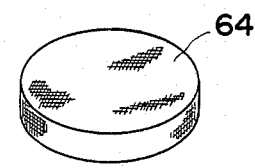
Figure 6A:
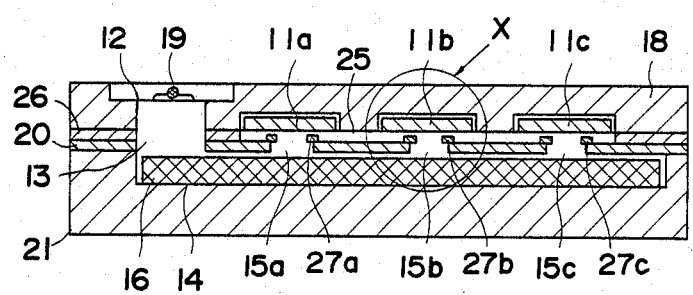
FIG. 6-A is an elevational section view illustrating an example of the ion activity measuring device according to the second embodiment of the invention.
Figure 6B:
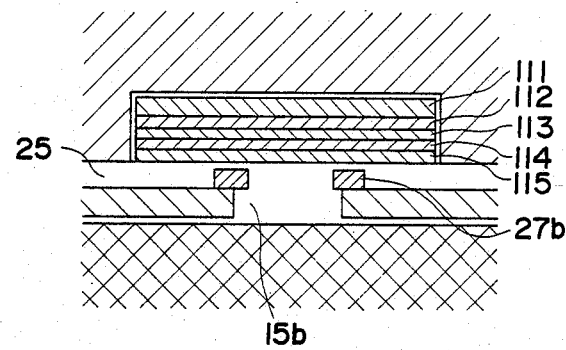
Figure 6C:
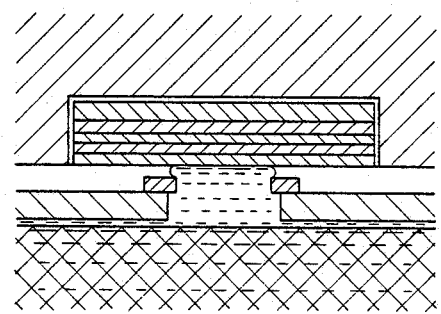
Figure 6D:
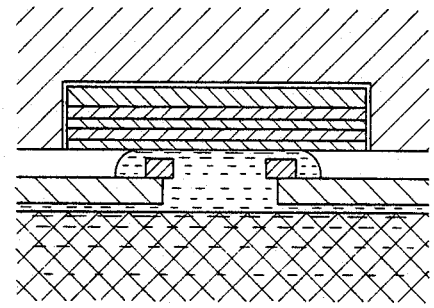
Figure 6E:
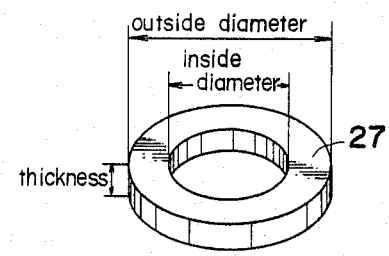

FIG. 5-A is an enlarged view illustrating the liquid coming into contact with the ion-selective electrode in a further example of the ion activity measureing device according to the first embodiment of the invention; and FIG. 5-B is a perspective view illustrating a porous distributor used in FIG. 5-A.

As shown in FIG. 5-A and FIG. 5-B, a porous distributor 64 may be provided within the space on the upper side of the upward passage in the first embodiment shown in FIG. 1 to FIG. 4.

FIG. 6-A is an elevational section view illustrating an example of the ion activity measuring device according to the second embodiment of the invention; FIG. 6-B is an enlarged view of a portion X enclosed with a circle in the elevational section of FIG. 6-A; FIG. 6-C is an enlarged view illustrating one state that the liquid is coming into contact with the ion-selective electrode; FIG. 6-D is an enlarged view illustrating another state that the liquid is coming into contact with the ion-selective electrode; and FIG. 6-E is a perspective view illustrating a spotting guide passage in the second embodiment of the invention.

Figure 7:
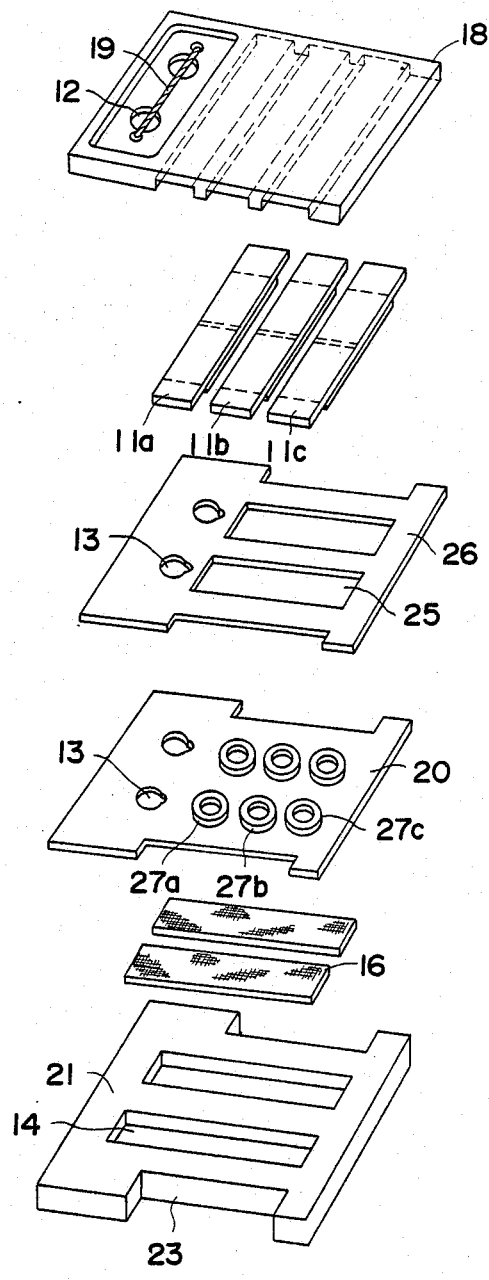
FIG. 7 shows each member of the ion activity measuring device of FIG. 6-A, in order to illustrate each member constituting the ion activity measuring device in more detail.

FIG. 7 shows each member of the ion activity measuring device of FIG. 6-A, in order to illustrate each member constituting the ion activity measuring device in more detail.

The perspective view and the bottom view illustrating the example of the ion activity measuring device according to the second embodiment of the invention are similar to FIG. 1 and FIG. 1-B, respectively.

As shown in FIG. 6-A, a liquid-guiding portion for guiding a reference liquid or a liquid sample to the surface of the ion-selective membrane comprises a liquid receiving opening 12 on the upper side, a downward passage 13 for conveying the liquid downwardly to the lower level under the surface of the ion-selective membrane, a horizontal passage 14 for conveying the liquid in the horizontal direction just below the surface of the ion-selective membrane, and upward passages 15a, 15b and 15c for conveying the liquid upwardly to the surface of the ion-selective membrane.

The upward passages 15a, 15b and 15c have the side wall provided under the condition that no capillary phenomenon to the surface of the ion-selective membrane occurs in a clearance between the top of said side wall and the surface of the ion-selective membrane. As shown in FIG. 6-A and FIG. 6-B, space 25 which is larger than the upward passages 15a, 15b and 15c is provided on the upper side against the upward passage. In the space 25, spotting guide passages 27a, 27b and 27c are provided on opening portions corresponding to the upward passages. As shown in FIG. 6-C, the liquid conveyed upwardly from the horizontal passage 14 then reaches the surface of the ion-selective membrane without capillary phenomenon guided by the spotting guide passages. When a condition such as the surface tension of the liquid, the quality or state of the ion selective membrane, or time after the liquid spotting is different from that in FIG. 6-C, as shown in FIG. 6-D, the liquid expands into the space 25. Accordingly, the liquid can be prevented by the spotting guide passages 27a, 27b, 27c and the space 25 from spreading on the surface of the ion-selective membrane caused by capillary phenomenon.

The space 25 is connected with all of the spotting guide passages 27a, 27b and 27c. The space 25 may be made open to the outside of the device through a passage other than the upward passage in this invention.

For performing smooth conveyance of the liquid, the horizontal passage 14 is preferably equipped with a porous distributor 16 (namely, liquid-conveying member having continuous micropores capable of showing capillarity) such as cotton bandage fabric, cotton gauze or nonwoven fabric. The employment of the porous distributor is particularly advantageous especially when the amount of the reference liquid or liquid sample is small.

The three pairs of ion-selective electrodes 11a, 11b and 11c are contained in the top frame 18 of plastic material, and generally fixed to the top frame. The top frame 18 has openings 12 to receive spotting of liquid therethrough, and said two openings (opening for a reference liquid and an opening for a liquid sample) are traversed by a bridge 19 such as a combustible thread bridge of polyethylene terephthalate fiber (e.g., spun yarn) to electrically connect both liquids of the reference liquid and the liquid sample to each other.

Around each of the openings 12 is provided a protruded region (not shown in the figures) which serves to prevent the liquid from flowing over the opening and also serves to easily receive spotting the liquid without fail.

Under the top frame 18 is provided an upper middle frame (spacer) 26. In the upper middle frame 26, a part of the downward passage 13 for downwardly conveying the spotted liquid and the space 25 provided on the upper side of the upward passage are formed as opening portions.

Under the upper middle frame 26 is provided a lower middle frame 20 of water-impermeable sheet such as a mask of plastic material. In the lower middle frame 20, a part of the downward passage 13 for downwardly conveying the spotted liquid and the upward passages 15a, 15b and 15c (under spotting guide passages 27a, 27b and 27c; not shown in FIG. 7) are formed as opening portions.

Spotting guide passages 27a, 27b and 27c are provided on the lower middle frame 20. In the spotting guide passage, inside space which has a function to guide the liquid is formed. An example of the spotting guide passage is a ring shown in FIG. 6-E. The thickness of the spotting guide passage is identical to the height of the space 25 or less. The diameter of the inside space (inside diameter shown in FIG. 6-E) is preferably that of the upward passage or less. When the inside diameter is same as the diameter of the upward passage, the spotting guide passage and the water-impermeable lower middle frame may be formed as an integrated structure so as to make the inside surface of the spotting guide passage and the upward passage a smooth curved surface. Outside diameter of the spotting guide passage shown in FIG. 6-E is arranged to make the spotting guide passage within the outline of the ion-selective membrane.

The spotting guide passages may be combined with the water-impermeable lower middle frame by the use of an adhesive. The spotting guide passage and the water-impermeable lower middle frame also may be formed as an integrated structure.

The upper middle frame 26 and the water-impermeable lower middle frame 20 are desired to be combined with the bottom surface of the top frame 18 by the use of an adhesive (e.g., pressure-sensitive adhesive or heat-sensitive adhesive) or through thermal bonding or physical engagement.

Bottom frame 21, horizontal passage 14, porous distributor 16, cutout portions 23, electricity-connecting regions 22a, 22b and 22c are similar to the first embodiment shown in FIG. 1 to FIG. 5.

Whole of the top frame, upper middle frame, water-impermeable lower middle frame, spotting guide passage and bottom frame, or a part of those frames can be formed as an integrated structure, as far as the ion-selective electrode and the porous distributor which is optionally employed can be contained therein. Each of the top frame, upper middle frame, lower middle frame, spotting guide passage and bottom frame is not always necessarily an integrated form, and can be composed of plural members In the device for measuring ion activity shown in FIG. 6-A to FIG. 7, the ion-selective electrode sheet is settled in a container comprising a top frame having opening portions which are located to correspond to each liquid receiving opening, an upper middle frame having opening portions which are located to correspond to each liquid receiving opening and to the upper opening of the upward passage, said opening portions corresponding to the upper opening of the upward passage being larger than said upper opening to avoid being in contact with the liquid, a water-impermeable lower middle frame having opening portions which are located to correspond to the downward and upward passages, said water-impermeable lower middle frame also having the spotting guide passage provided on said opening portions corresponding to the upward passages, and a bottom frame having a groove for forming the horizontal passage; and said bridge is fixed onto the top frame so as to traverse the opening portions of the top frame.

Figure 8:
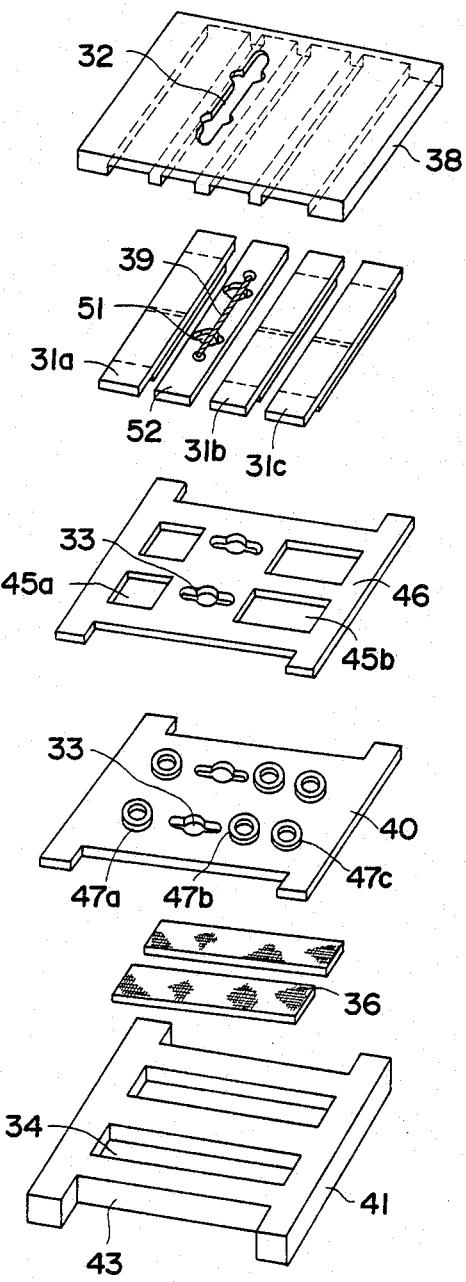
FIG. 8 shows each member of another example of the ion activity measuring device according to the second embodiment of the invention likewise in FIG. 7.

FIG. 8 shows each member of another example of the ion activity measuring device according to the second embodiment of the invention likewise in FIG. 7.

In the ion activity measuring device shown in FIG. 8, as well as in FIG. 7, three pairs of ion-selective electrode sheets 31a, 31b and 31c which are provided with ion-selective membranes on the top portion are arranged upside down to position the ion-selective membranes on the lowest side. The three pairs of ion-selective electrodes 31a, 31b and 31c are contained in a top frame 38 of plastic material, and generally fixed to the top frame. The top frame 38 has a liquid-receiving opening 32.

In the example of FIG. 8, the three pairs of ion-selective electrodes are divided into one pair and two pairs in the left side and the right side, respectively. The ion activity measuring device having such structure is very advantageous especially when a liquid having high viscosity such as whole blood is employed as a liquid sample, because the distance between the opening 32 and the farthest ion-selective electrode therefrom is shorter as compared with the device shown in FIGS. 6-A to FIG. 7.

Under the top frame 38 is placed a bridge-supporting member 52 of plastic material having two opening portions 51 in such a manner that the two opening portions 52 are located to correspond to the liquid receiving opening 32. The two opening portions are traversed by a bridge 39 to electrically connect both liquids of reference liquid and liquid sample spotted to the opening portions to each other. The bridge-supporting member of plastic material shown in FIG. 8 has substantially the same size as that of the above-mentioned one pair of ion-selective electrode.

Under the bridge-supporting member 52 is provided an upper middle frame 46. In the upper middle frame sheet 46, a part of a downward passage 33 for conveying a liquid downwardly and the space 45a and 45b provided on the upper side against the upward passage are formed as opening portions.

Under the upper middle frame 46 is provided a lower middle frame 40 of water-impermeable sheet such as a mask of plastic material. In the water-impermeable middle frame sheet 40, a part of a downward passage 33 for conveying a liquid downwardly and upward passages 35a, 35b and 35c (under spotting guide passages 47a, 47b and 47c; not shown in FIG. 8) are formed as opening portions. Spotting guide passages 47a, 47b and 47c are provided on the lower middle frame 40. The details of the space 45a, 45b, the upward passages 35a, 35b and 35c, and the spotting guide passages 47a, 47b and 47c are similar to that shown in FIG. 6-A to FIG. 6-E.

The upper middle frame 46 and the water-impermeable lower middle frame 40 are preferably combined with the lower surfaces of the bridge-supporting member 52 and the top frame 38 by the use of an adhesive (e.g., pressure-sensitive adhesive or heat-sensitive adhesive) or through thermal bonding or physical engagement.

Bottom frame 41, horizontal passage 34, porous distributor 36, cutout portions 43, electricity-connecting regions 42a, 42b and 42c are similar to the first embodiment shown in FIG. 1 to FIG. 5.

Whole of the top frame, bridge-supporting member, upper middle frame and water-impermeable lower middle frame, or a part of those frames can be formed as an integrated structure, as far as the ion-selective electrode and the porous distributor which is optionally employed can be contained therein. Each of the top frame, upper middle frame, lower middle frame and bottom frame can be composed of plural members, and any material can be optionally employed for those frames, as well as in the aforementioned example.

In the device for measuring ion activity shown in FIG. 8, the ion-selective electrode sheet is settled in a container comprising a top frame having opening portions which are located to correspond to each liquid receiving opening, a bridge-supporting member having opening portions which are located to correspond to the opening portions of the top frame, an upper middle frame having opening portions which are located to correspond to each liquid receiving opening and to the upper opening of the upward passage, said opening portions corresponding to the upper opening of the upward passage being larger than said upper opening to avoid being in contact with the liquid, a water-impermeable lower middle frame having opening portions which are located to correspond to the downward and upward passages, said water-impermeable lower middle frame also having the spotting guide passage provided on said opening portions corresponding to the upward passages, and a bottom frame having a groove for forming the horizontal passage; and said bridge is fixed onto the bridge-supporting member so as to traverse the opening portions of the bridge-supporting member.

In the case of ion activity measuring device illustrated in FIG. 8, since the top frame and the bridge-supporting member are formed separately as stated above, each of those members has a simple structure, and hence it can be easily prepared.

Further, in the figure a thread bridge is fixed not to the top frame but to an independent bridge-supporting sheet (namely, bridge-supporting member) in the device shown in FIG. 8, and accordingly the top frame is not distorted in the procedure of thermal bonding with the thread bridge so as not to give the distortion to the ion-selective electrode. As a result, an ion activity measuring device can be prepared with high accuracy, whereby a device with high accuracy is obtained.

Figure 9:
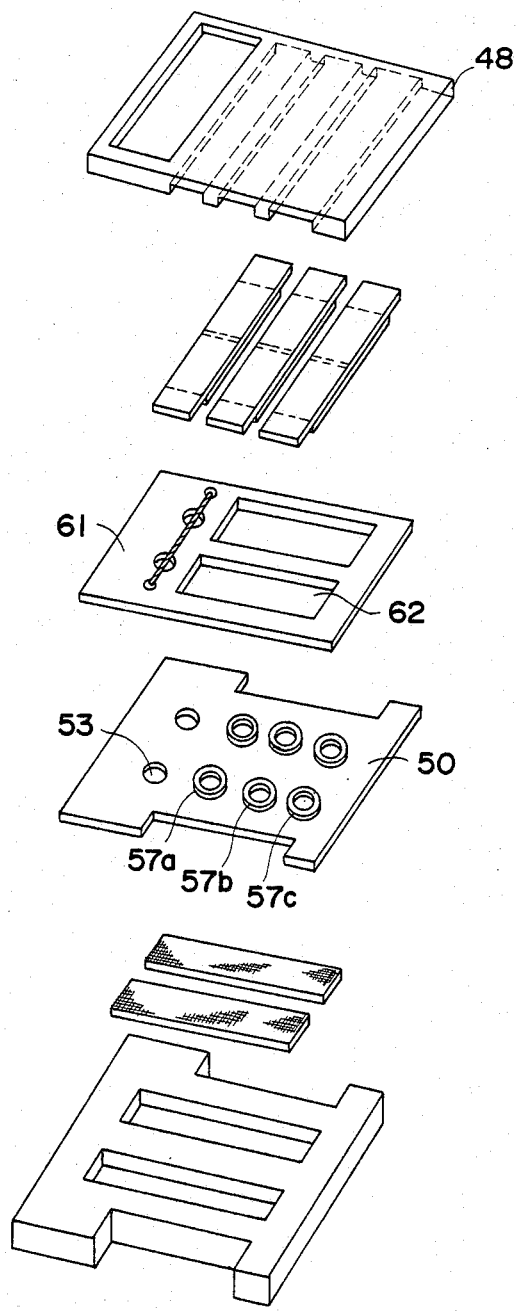
FIG. 9 shows each member of a further example of the ion activity measuring device according to the second embodiment of the invention likewise in FIG. 7 and 8.

FIG. 9 shows each member of an ion activity measuring device which is another more example of the devices according to the first embodiment of the invention, in order to illustrate each member constituting the ion activity measuring device in more detail, likewise in FIG. 7 and FIG. 8.

In the case of ion activity measuring device illustrated in FIG. 9, the top frame 48 and the bridge-supporting member 61 are formed separately likewise in the example shown in FIG. 8.

The bridge-supporting member 61 provides large space 62 corresponding to the space 25 shown in FIG. 6-A to FIG. 7. Accordingly, there is only one middle frame in example shown in FIG. 9, which is the water-impermeable middle frame 50 having opening portion 53 corresponding to the downward passage and other opening portions 55a, 55b and 55c corresponding to the upward passages.

In the device for measuring ion activity shown in FIG. 9, the ion-selective electrode sheet is settled in a container comprising a top frame having opening portions which are located to correspond to each liquid receiving opening, a bridge-supporting member having opening portions which are located to correspond to each liquid receiving opening and to the upper opening of the upward passage, said opening portions corresponding to the upper opening of the upward passage being larger than said upper opening to avoid being in contact with the liquid, a water-impermeable middle frame having opening portions which are located to correspond to the downward and upward passages, said water-impermeable middle frame also having the spotting guide passage provided on said opening portions corresponding to the upward passages, and a bottom frame having a groove for forming the horizontal passage; and said bridge is fixed onto the bridge-supporting member so as to traverse the opening portions of the bridge-supporting member.

Figure 10:
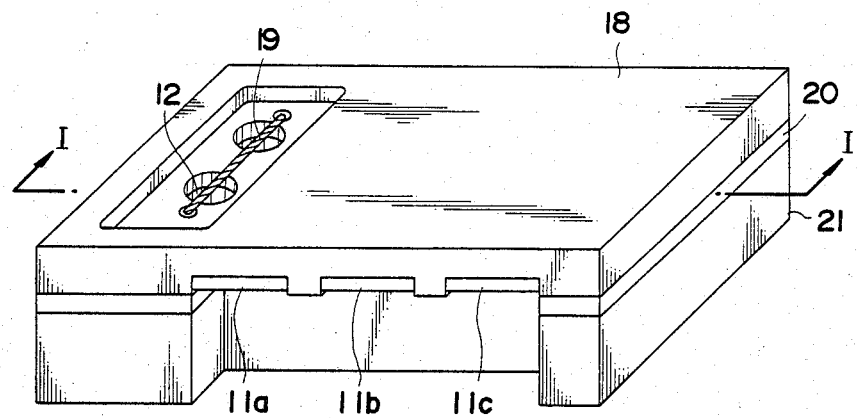
FIG. 10 is a perspective view illustrating an example of the ion activity measuring device according to the third embodiment of the invention.
Figure 10A:
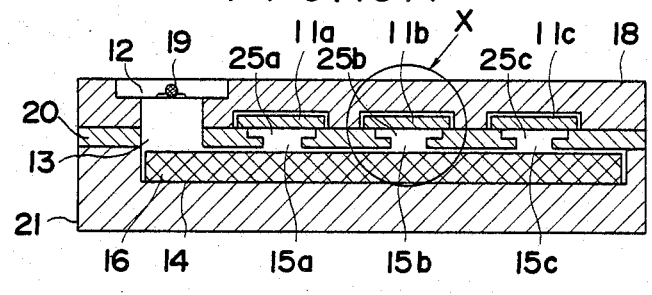
Figure 10B:
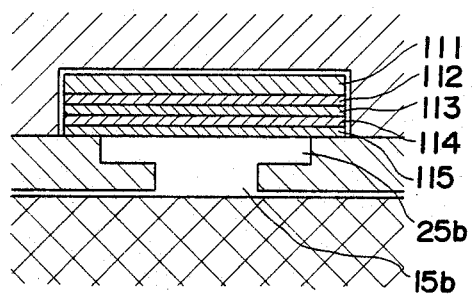
Figure 10C:
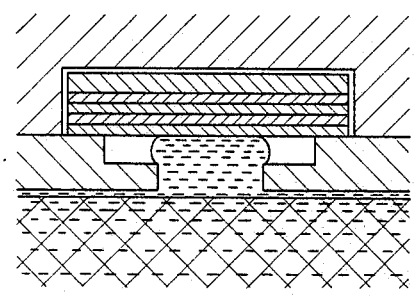

FIG. 10 is a perspective view illustrating an example of the ion activity measuring device according to the third embodiment of the invention. FIG. 10-A is an elevational section of the ion activity measuring device of FIG. 10 taken on line I-I; FIG. 10-B is an enlarged view of a portion X enclosed with a circle in the elevational section of FIG. 10-A; and FIG. 10-C is an enlarged view illustrating the liquid coming into contact with the ion-selective electrode.

Figure 11:
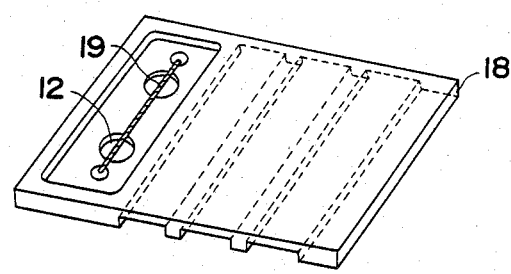
FIG. 11 shows each member of the ion activity measuring device of FIG. 10, in order to illustrate each member constituting the ion activity measuring device in more detail.
Figure 11:
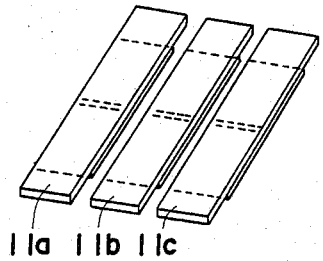
Figure 11:
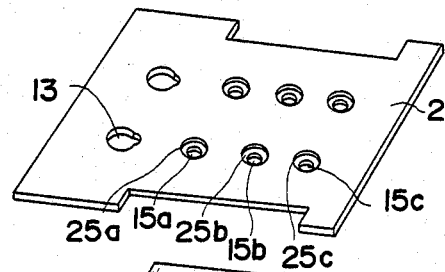
Figure 11:
Figure 11:
Figure 11:
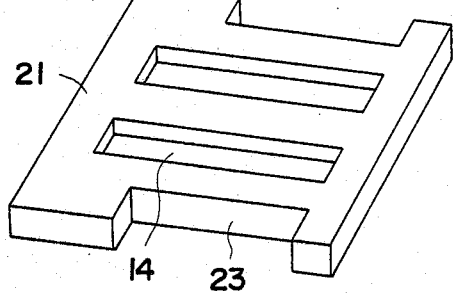
Figure 11:

FIG. 11 shows each member of the ion activity measuring device of FIG. 10, in order to illustrate each member constituting the ion activity measuring device in more detail.

The bottom view illustrating the example of the ion activity measuring device according to the third embodiment of the invention is similer to FIG. 1-B.

In the ion activity measuring device shown in the above-described figures, three pairs of ion-selective electrode sheets 11a, 11b and 11c, each sheet comprising ion-selective membranes on the top portion, are arranged upside down in such a manner that the ion-selective membranes are arranged on the lowest side. Each pair of ion-selective electrodes is a combination of an ion-selective electrode for a reference liquid and an ion-selective electrode for a liquid sample which are electrically insulated from each other. The ion-selective electrode sheet comprises, for instance, a support of plastic sheet 111, a metallic silver-deposited layer 112, a silver chloride layer 113, an electrolyte layer 114 and an ion-selective membrane 115, superposed in this order, as shown in FIG. 10-B. The ion-selective electrode sheet having such structure is placed upside down in the ion activity measuring device.

As shown in FIG. 10-A, a liquid-guiding portion for guiding a reference liquid or a liquid sample to the surface of the ion-selective membrane consists of a liquid receiving opening 12 on the upper side, a downward passage 13 for conveying the liquid downwardly to the lower level under the surface of the ion-selective membrane, a horizontal passage 14 for conveying the liquid in the horizontal direction to the position just below the surface of the ion-selective membrane, and upward passages 15a, 15b and 15c for conveying the liquid upwardly to the surface of the ion-selective membrane.

The upward passages 15a, 15b and 15c have the side wall being clear of the surface of the ion-selective membrane under the condition that no capillary phenomenon occurs in the clearance between the top of said side wall and the surface of the ion-selective membrane. As shown in FIG. 10-A and FIG. 10-B, spotting guide passages 25a, 25b and 25c are provided on opening portions corresponding to the upward passages, and the top of the side wall of the spotting guide passage is in contact with the surface of the ion-selective membrane 115. As shown in FIG. 10-C, the liquid conveyed upwardly from the horizontal passage 14 then reaches the surface of the ion-selective membrane without capillary phenomenon guided by the spotting guide passages. Accordingly, the liquid can be prevented by the spotting guide passages 25a, 25b, 25c from spreading on the surface of the ion-selective membrane caused by capillary phenomenon, so that the liquid can be also prevented from leaking out.

For performing smooth conveyance of the liquid, the horizontal passage 14 is preferably equipped with a porous distributor 16 (namely, liquid-conveying member having continuous micropores capable of showing capillarity) such as cotton bandage fabric, cotton gauze or nonwoven fabric. The employment of the porous distributor is particularly advantageous especially when the amount of the reference liquid or liquid sample is small.

The three pairs of ion-selective electrodes 11a, 11b and 11c are contained in the top frame 18 of plastic material, and generally fixed to the top frame. The top frame 18 has openings 12 to receive spotting of liquid therethrough, and said two openings (opening for a reference liquid and an opening for a liquid sample) are traversed by a bridge 19 such as a combustible thread bridge of polyethylene terephthalate fiber (e.g., spun yarn) to electrically connect both liquids of the reference liquid and the liquid sample to each other.

Around each of the openings 12 is provided a protruded region (not shown in the figures) which serves to prevent the liquid from flowing over the opening and also serves to easily receive spotting the liquid without fail.

Under the top frame 18 is provided a middle frame 20 of water-impermeable sheet such as a mask of plastic material. In the middle frame 20, a part of the downward passage 13 for downwardly conveying the spotted liquid and the upward passages 15a, 15b and 15c are formed as opening portions. The opening portions corresponding to the upward passages having a step inside so as to make the diameter of the upper opening than that of the lower opening, so that the openings are divided into the upward passages 15a, 15b, 15c and spotting guide passages 25a, 25b and 25c.

The water-impermeable middle frame 20 is desired to be combined with the bottom surface of the top frame 18 by the use of an adhesive (e.g., pressure-sensitive adhesive or heat-sensitive adhesive) or through thermal bonding or physical engagement.

Bottom frame 21, horizontal passage 14, porous distributor 16, cutout portions 23, electricity-connecting regions 22a, 22b and 22c are similar to the first embodiment shown in FIG. 1 to FIG. 5.

Whole of the top frame, water-impermeable middle frame, spotting guide passage and bottom frame, or a part of those frames can be formed as an integrated structure, as far as the ion-selective electrode and the porous distributor which is optionally employed can be contained therein. Each of the top frame, middle frame, spotting guide passage and bottom frame is not always necessarily an integrated form, and can be composed of plural members.

In the device for measuring ion activity shown in FIG. 10 and FIG. 11, the ion-selective electrode sheet is settled in a container comprising a top frame having opening portions which are located to correspond to each liquid receiving opening, a water-impermeable middle frame having opening portions which are located to correspond to the downward and upward passages, said opening portions corresponding to the upward passages having a step inside so as to make the diameter of the upper opening of the upward passage larger than that of the lower opening of the upward passage, and a bottom frame having a groove for forming the horizontal passage; and said bridge is fixed onto the top frame so as to traverse the opening portions of the top frame.

Figure 12:
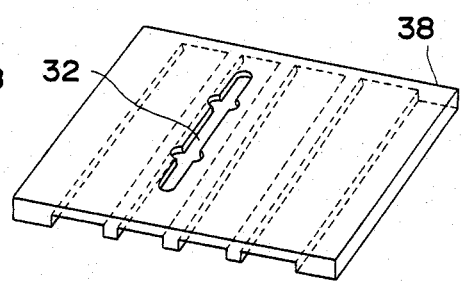
FIG. 12 shows each member of another example of the ion activity measuring device according to the third embodiment of the invention likewise in FIG. 11.
Figure 12:
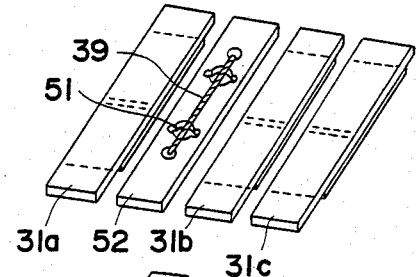
Figure 12:
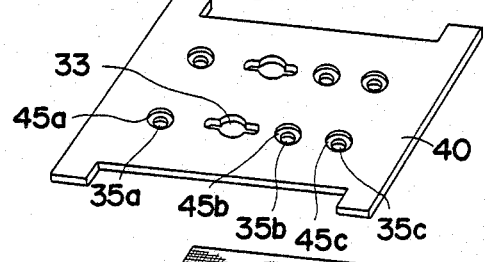
Figure 12:
Figure 12:
Figure 12:
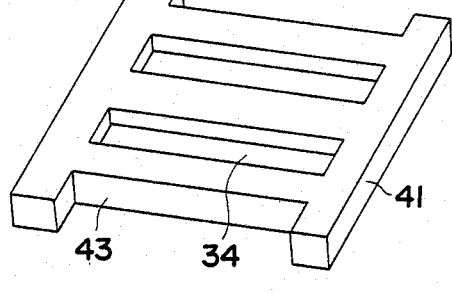
Figure 12:

FIG. 12 shows each member of another example of the ion activity measuring device according to the third embodiment of the invention likewise in FIG. 11.

In the ion activity measuring device shown in FIG. 12, as well as in FIG. 11, three pairs of ion-selective electrode sheets 31a, 31b and 31c which are provided with ion-selective membranes on the top portion are arranged upside down to position the ion-selective membranes on the lowest side. The three pairs of ion-selective electrodes 31a, 31b and 31c are contained in a top frame 38 of plastic material, and generally fixed to the top frame. The top frame 38 has a liquid-receiving opening 32.

In the example of FIG. 12, the three pairs of ion-selective electrodes are divided into one pair and two pairs in the left side and the right side, respectively. The ion activity measuring device having such structure is very advantageous especially when a liquid having high viscosity such as whole blood is employed as a liquid sample, because the distance between the opening 32 and the farthest ion-selective electrode therefrom is shorter as compared with the device shown in FIGS. 10 to 11.

Under the top frame 38 is placed a bridge-supporting member 52 of plastic material having two opening portions 51 in such a manner that the two opening portions 52 are located to correspond to the liquid receiving opening 32. The two opening portions are traversed by a bridge 39 to electrically connect both liquids of reference liquid and liquid sample spotted to the opening portions to each other. The bridge-supporting member of plastic material shown in FIG. 12 has substantially the same size as that of the above-mentioned one pair of ion-selective electrode.

Under the bridge-supporting member 52 is provided a middle frame 40 of water-impermeable sheet such as a mask of plastic material. In the water-impermeable middle frame sheet 40, a part of a downward passage 33 for conveying a liquid downwardly and upward passages 35a, 35b and 35c are formed as opening portions. The opening portions corresponding to the upward passages having a step inside so as to make the diameter of the upper opening than that of the lower opening, so that the openings are divided into the upward passages 35a, 35b, 35c and spotting guide passages 45a, 45b and 45c. The details of the upward passages 35a, 35b and 35c, and the spotting guide passages 45a, 45b and 45c are similar to that shown in FIG. 10 and FIG. 11.

The water-impermeable iddle frame 40 is preferably combined with the lower surfaces of the bridge-supporting member 52 and the top frame 38 by the use of an adhesive (e.g., pressure-sensitive adhesive or heat-sensitive adhesive) or through thermal bonding or physical engagement.

Bottom frame 41, horizontal passage 34, porous distributor 36, cutout portions 43, electricity-connecting regions 42a, 42b and 42c are similar to the first embodiment shown in FIG. 1 to FIG. 5.

Whole of the top frame, bridge-supporting member, water-impermeable middle frame and bottom frame, or a part of those frames can be formed as an integrated structure, as far as the ion-selective electrode and the porous distributor which is optionally employed can be contained therein. Each of the top frame, middle frame and bottom frame can be composed of plural members, and any material can be optionally employed for those frames, as well as in the aforementioned example.

In the device for measuring ion activity shown in FIG. 12, the ion-selective electrode sheet is settled in a container comprising a top frame having opening portions which are located to correspond to each liquid receiving opening, a bridge-supporting member having opening portions which are located to correspond to the opening portions of the top frame, a water-impermeable middle frame having opening portions which are located to correspond to the downward and upward passages, said opening portions corresponding to the upward passages having a step inside so as to make the diameter of the upper opening of the upward passage larger than that of the lower opening of the upward passage, and a bottom frame having a groove for forming the horizontal passage; and said bridge is fixed onto the bridge-supporting member so as to traverse the opening portions of the bridge-supporting member.

In the case of ion activity measuring device illustrated in FIG. 12, since the top frame and the bridge-supporting member are formed separately as stated above, each of those members has a simple structure, and hence it can be easily prepared.

Further, in the figure a thread bridge is fixed not to the top frame but to an independent bridge-supporting sheet (namely, bridge-supporting member) in the device shown in FIG. 12, and accordingly the top frame is not distorted in the procedure of thermal bonding with the thread bridge so as not to give the distortion to the ion-selective electrode. As a result, an ion activity measuring device can be prepared with high accuracy, whereby a device with high accuracy is obtained.

FIGS. 1 to 12 illustrate representative examples of the ion activity measuring device according to the present invention, but those examples by no means restrict the invention. For instance, an ion activity measuring device having a structure comprising characteristic constitutional elements of FIGS. 1 to 12 combined with each other is a preferred embodiment of the ion activity measuring device according to the invention. Further, the spotting of the sample liquid or reference liquid can be directly done onto a portion at the level lower than the surface of the ion-selective membrane.

The material of the bridge and the porous distributor in the device of the invention can be appropriately selected from materials having continuous micropores capable of showing capillarity (namely, porous material). As the porous material employable for the bridge, there can be mentioned a membrane filter, a conventional filter paper and a filter paper laminated with hydrophobic organic polymer layers on the both sides as described in Japanese Patent Provisional Publication No. 55(1980)-20499, as well as a combustible thread. As the the material employable for the porous distributor, there can be mentioned a variety of materials such as a combustible woven fabric, a combustible knit fabric, a membrane filter and a filter paper, as well as a cotton bandage fabric, a cotton gauze and a nonwoven fabric.

We claim:

1. In a method of measuring ion activity of a liquid sample comprising the steps of contacting a reference liquid and the liquid sample with surfaces of ion-selective membranes, respectively, of at least a pair of ion-selective electrode sheets which are electrically insulated from each other, said ion-selective membranes being arranged on one side of said ion-selective electrode sheets; and measuring a potential difference between said both ion-selective electrodes under the condition that said both liquid are electrically connected to each other by a bridge, the improvement which comprises each electrode sheet being positioned so as to have upward and downward-facing sides and the ion-selective membrane being arranged on the downward-facing side of the electrode sheet; and the contact being effected by spotting each liquid at a location proximate an area adjacent the upward-facing side; conveying the spotted liquid to a position below the surface of the ion-selective membrane and conveying the liquid upward to the surface of the membrane through an upward-oriented passage defined by a sidewall having upper and lower ends, said passage having an opening at the upper end, the opening being positioned to deliver the liquid to the surface of the membrane and said upper end being spaced apart from the surface of the membrane to provide a clearance therebetween, said clearance being sufficient to avoid capillary movement between the surface of the membrane and the upper end of the side wall.

2. The method of measuring ion activity as claimed in claim 1 wherein after the liquid is conveyed to a position below the surface and outside the perimeter of the area of the ion-selective membrane, the liquid is conveyed horizontally to a position just below the surface and within the area of the ion-selective membrane, and is then conveyed upwardly to the surface of the ion-selective membrane.

3. The method of measuring ion activity as claimed in claim 2 wherein the liquid is conveyed horizontally via a porous distributor.

4. The method of measuring ion activity as claimed in claim 1 wherein at least partial conveyance of said liquid in the upward direction is performed with a porous distributor.

5. The device for measuring ion activity as claimed in claim 1 wherein said ion-selective electrode sheet is positioned in a container comprising a top frame having opening portions which are located in registration with each liquid receiving opening, an upper middle frame having opening portions which are located in registration with each liquid receiving opening and the opening at the upper end of the upward-oriented passage, said opening portions corresponding to the opening at the upper end of the upward-oriented passage being larger than said upper end opening to avoid being in contact with the liquid, a water-impermeable lower middle frame having opening portions which are located in registration with the downward and upward passages, and a bottom frame having a groove for forming the horizontal passage; said bridge being fixed onto the top frame so as to traverse the opening portions of the top frame.

6. A device for measuring ion activity in a liquid sample comprising at least a pair of ion-selective electrode sheets having ion-selective membranes on the surface thereof, liquid-guiding portions for guiding a reference liquid and a liquid sample to each surface of said ion-selective membranes, respectively, and a bridge for electrically connecting both liquids to each other, the improvement which comprises each electrode sheet being positioned so as to have upward and downward-facing sides and the ion-selective membrane being arranged on the downward-facing side of the electrode sheet; said liquid-guiding portion comprises a liquid-receiving opening for supplying the liquid to a level lower than the surface of the ion-selective membrane, a horizontal passage for conveying the liquid in the horizontal direction to a position just below the area encompassed by the surface of the ion-selective membrane, and an upward-oriented passage defined by a side wall having upper and lower ends, said passage having an opening at the upper end, the opening being positioned to deliver the liquid to the surface of the membrane and said upper end being spaced apart from the surface of the membrane to provide a clearance therebetween, said clearance being sufficient to avoid capillary movement between the surface of the membrane and the upper end of the side wall.

7. The device for measuring ion activity as claimed in claim 6, wherein said horizontal passage is provided with a porous distributor.

8. The device for measuring ion activity as claimed in claim 6, wherein at least a portion of said upward-oriented passage contains a porous distributor.

9. The device for measuring ion activity as claimed in claim 6 having a space on the upper end of the upward-oriented passage, said space containing a porous distributor.

10. The device for measuring ion activity as claimed in claim 6 having a space on the upper end of the upward-oriented passage, said space being open to the outside of the device through a passage other than the upward-oriented passage.

11. The device for measuring ion activity as claimed in claim 6 wherein said ion-selective electrode sheet is positioned in a container comprising a top frame having opening portions which are in registration with each liquid receiving opening, a bridge-supporting member having opening portions which are located in registration with the opening portions of the top frame, an upper middle frame having opening portions which are in registration with each liquid receiving opening and with the opening of the upper end of the upward-oriented passage, said opening portions in registration with the opening of the upper end of the upward-oriented passage being larger than said upper opening to avoid being in contact with the liquid, a water-impermeable lower middle frame having opening portions which are located in registration with the downward and upward passages, and a bottom frame having a groove for forming the horizontal passage; said bridge being fixed onto the bridge-supporting member so as to traverse the opening portions of the bridge-supporting member.

12. The device for measuring ion activity as claimed in claim 6 wherein said ion-selective electrode sheet is positioned in a container comprising a top frame having opening portions which are located in registration with each liquid receiving opening, a bridge-supporting member having opening portions which are located in registration with each liquid receiving opening and the upper opening of the upward passage, said opening portions in registration with the upper opening of the upward passage being larger than said upper opening to avoid being in contact with the liquid, a water-impermeable middle frame having opening portions which are located to correspond to the downward and upward-oriented passages, and a bottom frame having a groove for forming the horizontal passage; and said bridge being fixed onto the bridge-supporting member so as to traverse the opening portions of the bridge-supporting member.

13. A device for measuring ion activity in a liquid sample comprising at least a pair of ion-selective electrode sheets having ion-selective membranes on the surface thereof, liquid-guiding portions for guiding a reference liquid and a liquid sample to each surface of said ion-selective membranes, respectively, and a bridge for electrically connecting both liquids to each other, the improvement which comprises each electrode sheet being positioned so as to have upward and downward-facing sides and the ion-selective membrane being arranged on the downward-facing side of the electrode sheet; said liquid-guiding portion comprises a liquid-receiving opening for supplying the liquid to a level lower than the surface of the ion-selective membrane, a horizontal passage for conveying the liquid in the horizontal direction to a position just below the area encompassed by the surface of the ion-selective membrane, and an upward-oriented passage defined by a side wall having upper and lower ends, said passage having an opening at the upper end, the opening being positioned to deliver the liquid to the surface of the membrane and said upper end being spaced apart from the surface of the membrane to provide a clearance therebetween, said clearance sufficient to avoid capillary movement between the surface of the membrane and the upper end of the side wall, and a spotting guide passage provided on the upper end of the upward-oriented passage, said spotting guide passage functioning to guide the liquid to the surface of the ion-selective membrane and preventing the liquid which has reached the surface of the ion-selective membrane from spreading to the side of the ion-selective membrane along said surface.

14. The device for measuring ion activity as claimed in claim 13 wherein said horizontal passage contains a porous distributor.

15. The device for measuring ion activity as claimed in claim 13 wherein said spotting guide passage is open to the outside of the device through a passage other than the upward-oriented passage.

16. The device for measuring ion activity as claimed in claim 13 wherein said ion-selective electrode sheet is positioned in a container comprising a top frame having opening portions which are located in registration with each liquid receiving opening, an upper middle frame having opening portions which are located in registration with each liquid receiving opening and with the opening at the upper end of the upward-oriented passage, said opening portions corresponding to the opening at the upper end of the upward-oriented passage being larger than said upper end opening to avoid being in contact with the liquid, a water-impermeable lower middle frame having opening portions which are located in registration with the downward and upward passages, said water-impermeable lower middle frame also having the spotting guide passage provided on said opening portions in registration with the upward passages, and a bottom frame having a groove for forming the horizontal passage; said bridge being fixed onto the top frame so as to traverse the opening portions of the top frame.

17. The device for measuring ion activity as claimed in claim 13 wherein said ion-selective electrode sheet is positioned in a container comprising a top frame having opening portions which are in registration with each liquid receiving opening, a bridge-supporting member having opening portions which are located in registration with the opening portions of the top frame, an upper middle frame having opening portions which are in registration with each liquid receiving opening and with the opening of the upper end of the upward-oriented passage, said opening portions in registration with the opening of the upper end of the upward-oriented passage being larger than said upper opening to avoid being in contact with the liquid, a water-impermeable lower middle frame having opening portions which are located in registration with the downward and upward passages, and a bottom frame having a groove for forming the horizontal passage; said water-impermeable lower middle frame also having the spotting guide passage provided on said opening portions corresponding to the upward-oriented passages, said bridge being fixed onto the bridge-supporting member so as to traverse the opening portions of the bridge-supporting member.

18. The device for measuring ion activity as claimed in claim 13 wherein said ion-selective electrode sheet is positioned in a container comprising a top frame having opening portions which are located in registration to each liquid receiving opening, a bridge-supporting member having opening portions which are located in registration with each liquid receiving opening and the upper opening of the upward passage, said opening portions in registration with the upper opening of the upward passage being larger than said upper opening to avoid being in contact with the liquid, a water-impermeable middle frame having opening portions which are located to correspond to the downward and upward-oriented passages, said water-impermeable middle frame also having the spotting guide passage provided on said opening portions corresponding to the upward-oriented passages, and a bottom frame having a groove for forming the horizontal passage; said bridge being fixed onto the bridge-supporting member so as to traverse the opening portions of the bridge supporting member.

19. A device for measuring ion activity in a liquid sample comprising at least a pair of ion-selective electrode sheets having ion-selective membranes on the surface thereof, liquid-guiding portions for guiding a reference liquid and a liquid sample to each surface of said ion-selective membranes, respectively, and a bridge for electrically connecting both liquids to each other, the improvement which comprises each electrode sheet being positioned so as to have upward and downward-facing sides and the ion-selective membrane is arranged on the downward-facing side of the electrode sheet; said liquid-guiding portion comprises a liquid-receiving opening for supplying the liquid to a level lower than the surface of the ion-selective membrane, a horizontal passage for conveying the liquid in the horizontal direction to a position just below the area encompassed by the surface of the ion-selective membrane, and an upward-oriented passage defined by a side wall having upper and lower ends, said passage having an opening at the upper end, the opening being positioned to deliver the liquid to the surface of the membrane and said upper end being spaced apart from the surface of the membrane to provide a clearance therebetween, said clearance sufficient to avoid capillary movement between the surface of the membrane and the upper end of the side wall, and a spotting guide passage provided on the upper end of the upward-oriented passage, said spotting guide passage functioning to guide the liquid to the surface of the ion-selective membrane and preventing the liquid which has reached the surface of the ion-selective membrane from spreading to the side of the ion-selective membrane along said surface, the top of the side wall of said spotting guide passage being in contact with the surface of the ion-selective membrane.

20. The device for measuring ion activity as claimed in claim 19 wherein said ion-selective electrode sheet is positioned in a container comprising a top frame having opening portions which are in registration with each liquid receiving opening, a water-impermeable middle frame having opening portions with are in registration with the downward and upward-oriented passages, said opening portions corresponding to the upward-oriented passages having a step inside so as to make the diameter of the upper opening of the upward-oriented passage larger than that of the lower opening of the upward-oriented passage, and a bottom frame having a groove for forming the horizontal passage; said bridge being fixed onto the top frame so as to traverse the opening portions of the top frame.

21. The device for measuring ion activity as claimed in claim 20, wherein said horizontal passage contains a porous distributor.

22. The device for measuring ion activity as claimed in claim 19 wherein said ion-selective electrode sheet is positioned in a container comprising a top frame having opening portions which are in registration with each liquid receiving opening, a bridge-supporting member having opening portions which are in registration with the opening portions of the top frame, a water-impermeable middle frame having opening portions with are in registration with the downward and upward-oriented passages, said opening portions corresponding to the upward-oriented passages having a step inside so as to make the diameter of the upper opening of the upward-oriented passage larger than that of the lower opening of the upward-oriented passage, and a bottom frame having a groove for forming the horizontal passage; said bridge being fixed onto the top frame so as to traverse the opening portions of the top frame.

* * * * *